(12) United States Patent
Donald et al.

(10) Patent No.: US 9,931,151 B2
(45) Date of Patent: Apr. 3, 2018

(54) IMPACTOR AND REMOVER DEVICES

(71) Applicant: Archer Sciences, LLC, Colts Neck, NJ (US)

(72) Inventors: Gordon Donald, Eatontown, NJ (US); Arthur Alfaro, Colts Neck, NJ (US); Lawrence Kiefer, Newark, NJ (US); Kevin Strauss, Columbia, MD (US)

(73) Assignee: ARCHER SCIENCES, LLC, Colts Neck, NJ (US)

( * ) Notice: Subject to any disclaimer, the term of this patent is extended or adjusted under 35 U.S.C. 154(b) by 580 days.

(21) Appl. No.: 14/598,952

(22) Filed: Jan. 16, 2015

(65) Prior Publication Data

US 2015/0196343 A1    Jul. 16, 2015

Related U.S. Application Data

(60) Provisional application No. 61/928,011, filed on Jan. 16, 2014.

(51) Int. Cl.
| | |
|---|---|
| *A61B 17/92* | (2006.01) |
| *A61B 90/30* | (2016.01) |
| *A61B 17/00* | (2006.01) |
| *A61B 17/16* | (2006.01) |
| *A61B 90/00* | (2016.01) |

(52) U.S. Cl.
CPC .............. *A61B 17/92* (2013.01); *A61B 90/30* (2016.02); *A61B 17/1604* (2013.01); *A61B 17/1626* (2013.01); *A61B 2017/00119* (2013.01); *A61B 2017/00141* (2013.01); *A61B 2017/00199* (2013.01); *A61B 2017/00398* (2013.01); *A61B 2017/00734* (2013.01); *A61B 2017/924* (2013.01); *A61B 2090/064* (2016.02)

(58) Field of Classification Search
CPC . A61B 17/92; A61B 17/921; A61B 2017/924; A61B 2017/925; A61B 2017/927; A61B 2017/928
USPC ................................. 173/2, 40, 41, 216, 217
See application file for complete search history.

(56) References Cited

U.S. PATENT DOCUMENTS

| | | | |
|---|---|---|---|
| 6,520,266 B2 * | 2/2003 | Bongers-Ambrosius | B25D 11/12 173/115 |
| 6,868,918 B2 * | 3/2005 | Shinohara | B23Q 5/28 173/114 |

(Continued)

*Primary Examiner* — Eric S Gibson
(74) *Attorney, Agent, or Firm* — Timothy X. Gibson, Esq.; Gibson & Dernier LLP

(57) ABSTRACT

An impactor having a housing including an upper portion and a lower portion at least a part of which extends perpendicularly from the upper portion, a ram having a first end positioned in the upper portion and positioned in axial alignment with the lower portion, an opposite end of the ram extending from the lower portion of the housing, at least one drive assembly including a first drive shaft operably coupled to a cam shaft, a cam operably coupled to the cam shaft, a cam operably coupled to the cam shaft, the drive shaft operably connectable to motor, wherein the cam is operable to rotate and positioned to contact the proximal end of the ram upon rotation of the cam, a circuit board comprising circuitry operable to receive instructions from a plurality of switches electrically coupled to the circuit board to operate the impactor, wherein the impactor is operable to deliver low amplitude pulsed strikes to a workpiece at variable frequencies.

20 Claims, 14 Drawing Sheets

(56) References Cited

U.S. PATENT DOCUMENTS

| | | | | |
|---|---|---|---|---|
| 7,559,449 B2* | 7/2009 | Viola | A61B 17/128 | 227/130 |
| 7,637,327 B2* | 12/2009 | Grunig | A61B 17/162 | 173/90 |
| 7,708,739 B2* | 5/2010 | Kilburn | A61B 17/92 | 606/86 R |
| 8,336,752 B2* | 12/2012 | Viola | A61B 17/128 | 128/898 |
| 8,695,726 B2* | 4/2014 | Pedicini | A61B 17/1604 | 173/109 |
| 8,926,625 B2* | 1/2015 | Lebet | A61B 17/92 | 606/100 |
| 8,968,326 B2* | 3/2015 | Mani | A61F 2/4607 | 606/100 |
| 9,211,131 B2* | 12/2015 | Donnet | A61B 17/22004 | |
| 9,554,965 B2* | 1/2017 | Foehrenbach | A61B 17/22012 | |
| 2008/0275471 A1* | 11/2008 | Viola | A61B 17/128 | 606/142 |
| 2010/0137760 A1* | 6/2010 | Schulz | A61B 17/1697 | 601/108 |
| 2010/0170931 A1* | 7/2010 | Viola | A61B 17/128 | 227/175.1 |
| 2012/0172939 A1* | 7/2012 | Pedicini | A61B 17/1604 | 606/86 R |
| 2012/0215267 A1* | 8/2012 | Pedicini | A61B 17/92 | 606/86 R |
| 2013/0161050 A1* | 6/2013 | Pedicini | B25D 17/00 | 173/201 |
| 2014/0318823 A1* | 10/2014 | Pedicini | A61B 17/1604 | 173/201 |
| 2015/0196343 A1* | 7/2015 | Donald | A61B 17/92 | 606/100 |

* cited by examiner

IMPACTOR AND REMOVER DEVICES

CROSS-REFERENCE TO RELATED APPLICATIONS

This application claims the benefit of U.S. Provisional Application No. 61/928,011 filed Jan. 16, 2014, the entirety of which is incorporated herein by reference.

FIELD OF THE INVENTION

This invention relates to the field of impactors. More specifically it relates to medical device impactor instruments.

BACKGROUND

Surgery, more specifically orthopedic surgery, often requires the surgeon to apply significant forces to the anatomy in order to achieve a desired result. Insertion of medical devices, particularly orthopedic, typically involves repetitive low-frequency and high magnitude forces, commonly from a mallet or hammer. These high peak impact forces predispose the bone or soft tissue to mechanical failure or injury. Furthermore, high sudden peak forces make it more difficult to center the tool or implant.

For example, a surgeon may need to remove bony anatomy by chiseling. Chiseling typically requires at least two tools: a chisel with one bladed end perpendicular to the long axis of the instrument and the opposite end formed as a striking surface, and mallet used to apply force to the striking surface of the first tool.

In another application, a surgeon may need to impact a device in order to modify the anatomy to receive an implantable device. In the case of an orthopedic hip implant, a surgeon may repeatedly impact a broaching device to create the desired cavity within a femur. After an implantable device has been inserted, further impact may be necessary to position the device in its desired location or secure it in place.

In another application, a surgeon may need to insert a device into the anatomy. In orthopedics, examples include but are not limited to hip stems, knee replacements, shoulder replacements and various spinal devices such as interbody spacers, artificial disc replacements, interspinous devices and longitudinal members.

However, challenges exist when impacting or inserting devices, include surgeon fatigue, harm to the patient, harm to the device, whether it be the instrument or implant, and the need for multiple types of impactors or inserters depending on the type of surgery being performed.

The act of repeated striking an instrument with a mallet requires strength, endurance and accurate placement. In longer procedures, this activity could prematurely fatigue the user. Furthermore, when impacting with greater force or amplitude, the risk of harming the patient increases. In the example of hip replacement surgery, inserting a femoral stem under great force could fracture the femur. High amplitude impacting under lower frequency could also damage a medical implant. In the example of an Anterior Lumbar Interbody Fusion (ALIF) device, high amplitude impact forces could break the implantable device. Finally, in some instrument sets, each sample inserter may be a stand-alone device which adds weight, bulk and cost to the set. A mallet alone typically adds 2-5 pounds of weight to an instrument set.

Therefore, a need exists for a medical device impactor and inserter operable to apply consistent, controlled impact at a desired amplitude and frequency.

SUMMARY OF THE INVENTION

In accordance with one or more embodiments, medical impactors for surgical procedures are disclosed. The disclosed impactors are operable to apply consistent, controlled impact at a desired amplitude and frequency. The impactors are configured such that an actuating component will produce a repeatable force or pulse parallel to the long axis of the device. The repeated force or pulse may occur at least two times, at variable intervals, such as in short succession, and with a smaller amplitude, or force, than that of a surgical mallet operated by a surgical staff member.

In some embodiments impactors are disclosed which are operable to apply low amplitude, high frequency impact. Utilizing a high-frequency impacting device with low peak force provides for the same or greater total energy of delivery and markedly less risk of injury to the tissues and patient.

In further embodiments, devices are provided which may employ repetitive cyclic force greater than 2 Hz to facilitate driving, inserting, implanting, removing, relocating a device, implant or tool in bone or soft tissue for medical applications. High-frequency may be combined with static force or load. The forces applied may be axial or non-axial, translational or torsional. Devices disclosed herein may be used for orthopedic or non-orthopedic applications.

In some embodiments an impactor device is a stand-alone impactor. In another embodiment, the device is operable to receive one or more attachments, optionally interchangeably, that may be fitted to the distal end of a ram of the device.

In a further embodiment, an impactor device is disclosed which is operable to remove an implant.

In another embodiment, an impactor is disclosed which includes a housing having an upper portion and a lower portion, at least part of the lower portion extending perpendicularly from the upper portion, a ram having a first end positioned in the upper portion and positioned in axial alignment with the lower portion, an opposite end of the ram extending from the lower portion of the housing, at least one drive assembly having a first drive shaft operably coupled to a cam shaft, a cam operably coupled to the cam shaft, the drive shaft operably connectable to motor, wherein the cam is operable to rotate and positioned to contact the proximal end of the ram upon rotation of the cam, a circuit board including circuitry operable to receive instructions from a plurality of switches electrically coupled to the circuit board to operate the impactor, wherein the impactor is operable to deliver low amplitude pulsed strikes to a workpiece at variable frequencies.

The impactor may include at least one coil spring disposed annularly within the lower housing in which a portion of the ram is disposed in axial alignment within the coil spring. The impactor may include a battery electrically coupled to the circuit board.

In certain embodiments the impactor is a hand-held device.

In some embodiments the impactor includes at least one motor contained within the housing and operably coupled to the drive shaft. The motor may be an inserter motor electrically coupled to the circuit board and a battery or external power source, and operably coupled to the drive shaft, wherein the ram includes an inserter surface positioned to receive impact from the cam to drive the ram in the direction of the lower housing. This embodiment is useful for applications requiring insertion of an implant, chiseling, broaching and the like.

In other embodiments the motor may be a remover motor electrically coupled to the circuit board and a battery or external power source, and operably coupled to the drive shaft, wherein the ram comprises a removal flange positioned to receive impact from the cam to drive the ram in the direction of the upper housing. This embodiment is useful in applications requiring removal of an implant or other workpiece.

In yet further embodiments, the impactor includes an inserter motor and a remover motor electrically coupled to the circuit board, and further including at least two drive assemblies, wherein each of the inserter and remover motors are operably coupled to one of each at least two drive assemblies, wherein the ram includes an inserter surface positioned to receive impact from a first drive assembly cam to drive the ram in the direction of the lower housing, and wherein the ram includes a removal flange positioned to receive impact from a second drive assembly cam to drive the ram in the direction of the upper housing.

The impactor may include a plurality of switches. For example, the impactor may include one or more of a power switch, force selection switch, fire switch, continuous mode/single mode switch operable to control the rotation of a cam between a single rotation and continuous rotation, and/or a motor selection switch, each of which is electrically coupled to the circuit board.

The impactor may include one or more sensors or sets of sensors. In one embodiment the impactor includes a mounting plate mounted to the lower housing having an opening formed therein in which the ram is disposed, the mounting plate having at least one sensor electrically coupled to the circuit board, the at least one sensor operable to detect misalignment of the ram.

In other embodiments the impactor may include a sensor electrically coupled to the circuit board and positioned to detect force imparted by a cam on the ram. The impactor may include a sensor electrically coupled to the circuit board and positioned to detect force imparted by a user on the impactor.

The impactor in some embodiments includes a display electrically coupled to the circuit board operable to display data. The impactor may include a battery electrically coupled to the circuit board.

In some embodiments the ram includes a connecting element positioned at a distal end operable to connect a tool or implant.

In still a further embodiment, the impactor includes a drive assembly which includes a drive shaft having a connecting element disposed on an end opposite an end coupled to the cam shaft, the connecting element operable to connect the drive shaft to an external drive.

Various further features are disclosed in the drawings and description.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE INVENTION

Figure 1:
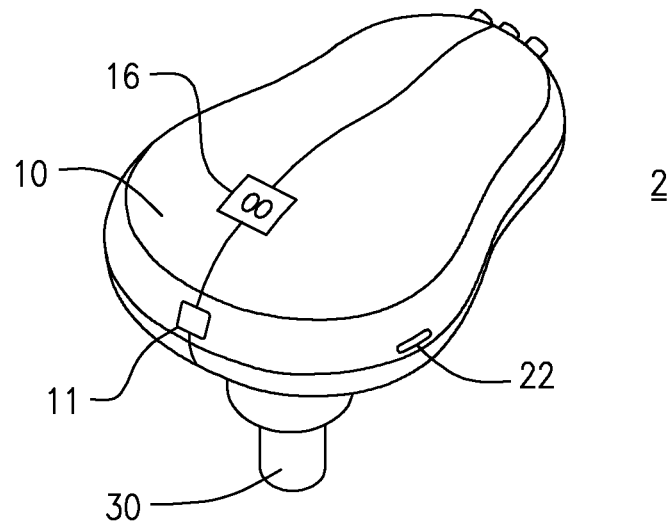
FIG. 1 is a top perspective view of a device according to an embodiment of the present disclosure.
Figure 1A:
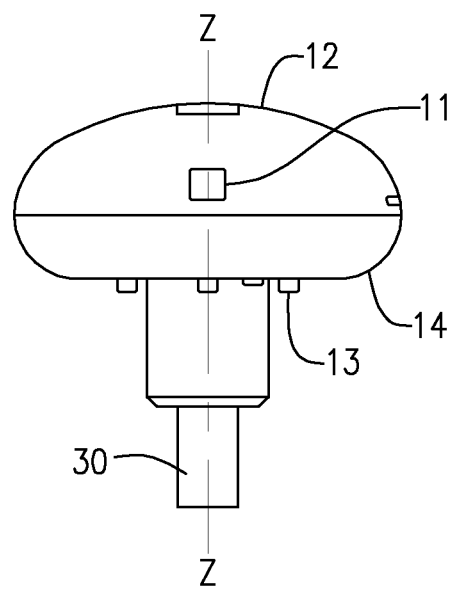
FIG. 1A is rear view of an embodiment of the device of FIG. 1.
Figure 1B:
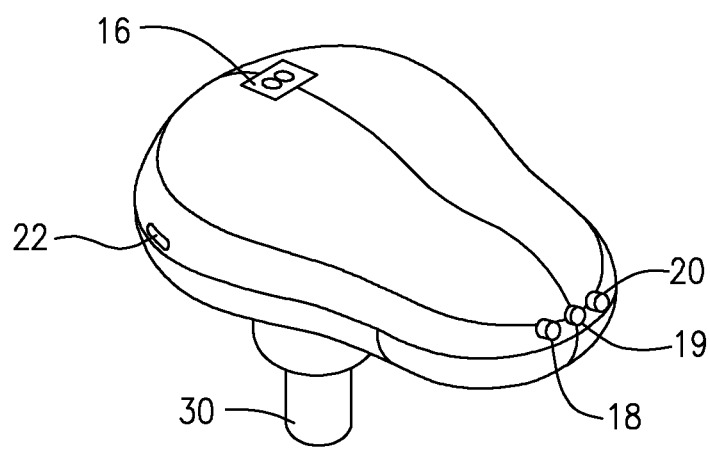
FIG. 1B is a side perspective view of the device according to FIG. 1.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. Unless otherwise indicated or defined, all technical and scientific terms used herein have the same meaning as commonly understood by one of ordinary skill in the art to which the invention pertains. The terminology used herein is for describing particular embodiments only and is not intended to be limiting.

Embodiments of the present invention are described with reference to the FIGS. Now referring to FIGS. 1-3, an impactor 2 operable to impart impact force and/or removal force includes a housing 10, display 16, ram 30, motors 40 and 46, cam shafts 50 and 54, cams 52 and 56, multifunction sensor 60, spring 70, mounting plate 80, strike alignment sensors 81 and circuit board 92. The impactor 2 may include a battery 90 to power the impactor 2. In other embodiments the impactor may use an external power source, such as AC power or an external drive.

The impactor 2 may be any size and dimension. In one embodiment the housing 10 is sized and dimensioned to fit comfortably in the hand of an adult user. The housing 10 may include upper and lower housing elements 12 and 14, respectively. In embodiments for a hand-held device, upper housing 12 includes an exterior surface that may be for example, and not by way of limitation, about 3-15 cm in width and about 3-20 cm in length. In other embodiments the exterior surface may be for example from 5-12 cm in width and 5-15 cm in length. The upper housing 12 may include a plurality of switches 11, 18, 19, 20 and 22, and one or more indicators 16 as described further herein below. It will be understood by those skilled in the art that the location, type and orientation of the switches may be varied depending on the configuration of the housing 10 and the arrangement of elements of the impactor 2. As shown, the upper housing 12 includes a display 16 such as but not limited to a LCD display operable to permit a user to monitor various functions of the device. The upper housing 12 includes force selection switch 18, power switch 19, continuous mode/single mode switch 20, stroke direction control switch 22, and fire switch 11. Upper housing 12 may further include mounts for cam shafts 50 and 54 and multifunction sensor 60.

Lower housing 14 houses ram 30 and spring 70 mounted annularly within a lower section of the lower housing 14. The lower housing 14 may include mounts for motors 40 and 46, mounting plate 80, battery 90 and circuit board 92 and electrical sensors tied into the circuit board 92. With further reference to FIG. 4, the lower housing 14 may include a work zone light 17 to illuminate a work area for a user.

It will be understood by those skilled in the art that the location, type and orientation of elements contained or mounted in the lower housing 14 may be varied depending on the configuration of the housing 10 and the arrangement of elements of the impactor 2.

The ram 30 is positioned and operable to move in a reciprocating fashion within the housing 10. Mounting plate 80 serves as a guide aligning the ram 30 in the housing 10 and also as a stop for spring 70. Fasteners 13 such as but not limited to screws may be employed to retain mounting plate 80 in position on housing 10. The ram 30 imparts force on a work piece, whether that work piece is an implant, tissue such as bone or the like. Ram 30 includes flanges 32, 33 and 37. Flange 32 is operably positioned to apply force to spring 70. It will be noted the impactor 2 may employ a single spring, as shown for example in FIG. 2, disposed such that flange 32 is positioned between coils of the spring. In other embodiments, two springs may be employed, with one spring positioned above the flange 32 and the other positioned below the flange 32, toward the distal end of the ram 30, i.e., the end of the ram 30 that is outside the housing 10. In either case, depending on the motor actuated for operation, i.e., the remover motor 46 or the inserter motor 42, the spring 70 is operable to restore the ram 30 to a starting, or baseline position after each cam rotation.

Flange 33 is positioned closer to the opposite end of the ram 30, adjacent the mounting plate 80.

Motors 40 and 46 may be any suitable motor. In one embodiment the motors 40 and 46 are universal motors which may employ speed control such as a centrifugal mechanism or resistance method. Universal motors offer the design choice of AC or DC power, have a high starting torque and variable speed characteristics.

Figure 2:
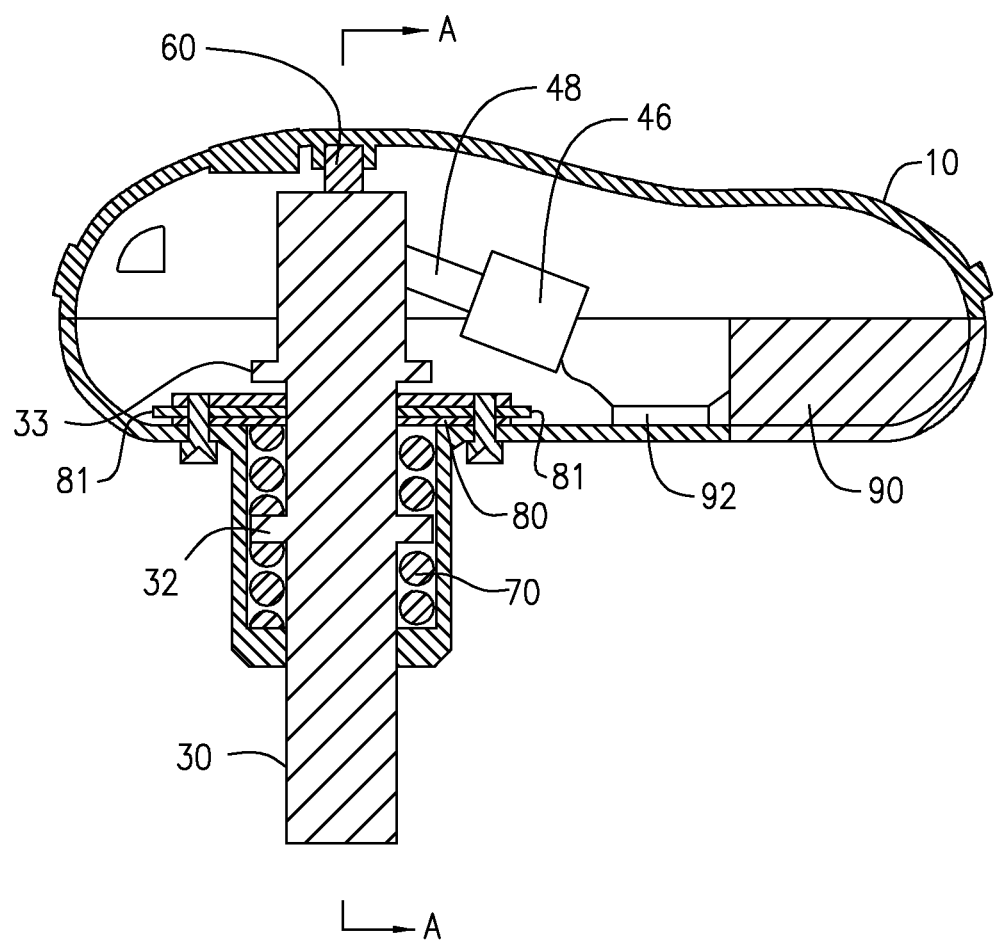
FIG. 2 is a cross-sectional view of the device according to FIG. 1A taken along line Z-Z according to an embodiment of the present disclosure.
Figure 3A:
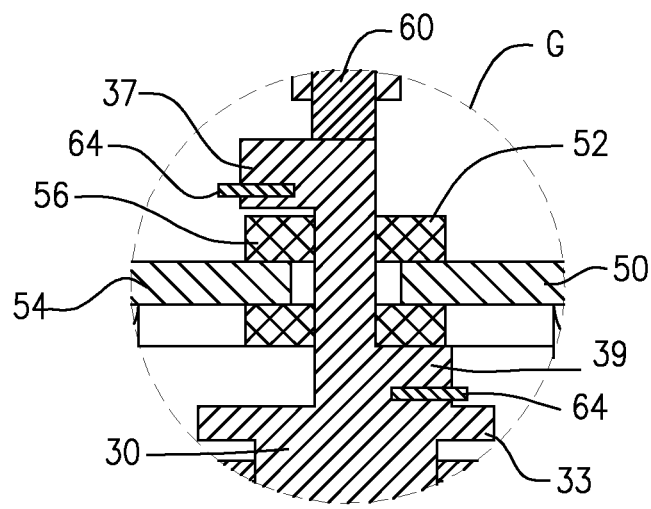
FIG. 3A is an enlarged view of detail G of FIG. 3 according to an embodiment of the present disclosure.
Figure 3:
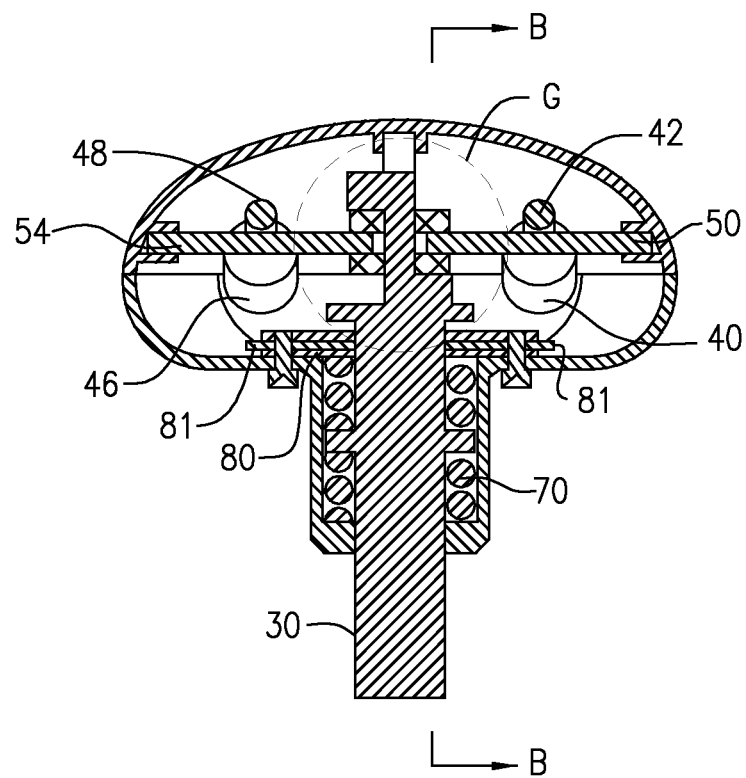
FIG. 3 is a cross-sectional view of the device according to FIGS. 1 and 1A, taken along the line A-A of FIG. 2.

With reference to FIG. 2, motor 46 is a remover motor, and includes drive shaft 48. With further reference to FIGS. 3 and 3A, drive shaft 48 is coupled to remover cam shaft 54, which is in turn is coupled to remover cam 56. When the remover motor 46 is actuated, remover cam 56 turns and a lobe thereof (which may include lobes identical to the lobes shown for inserter cam 52 in FIGS. 4 and 4A) strikes the ram removal flange 37, driving the ram 30 upward, providing a removing force. Spring 70 is compressible between mounting plate 80 and flange 32 upon upward force imparted by the remover cam 56. After a lobed portion of cam 56 passes through contact with the ram removal flange 37, the spring 70 restores the ram 30 to the baseline position, until a lobe of the remover cam 56 again strikes the ram removal flange 37, whereupon the removing force is repeated.

Figure 4A:
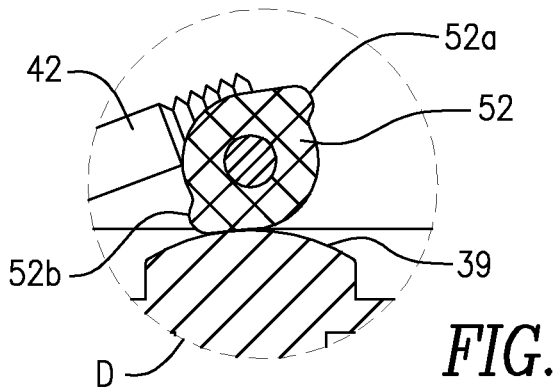
FIG. 4A is an enlarged view of detail D of FIG. 4 according to an embodiment of the present disclosure.
Figure 4:
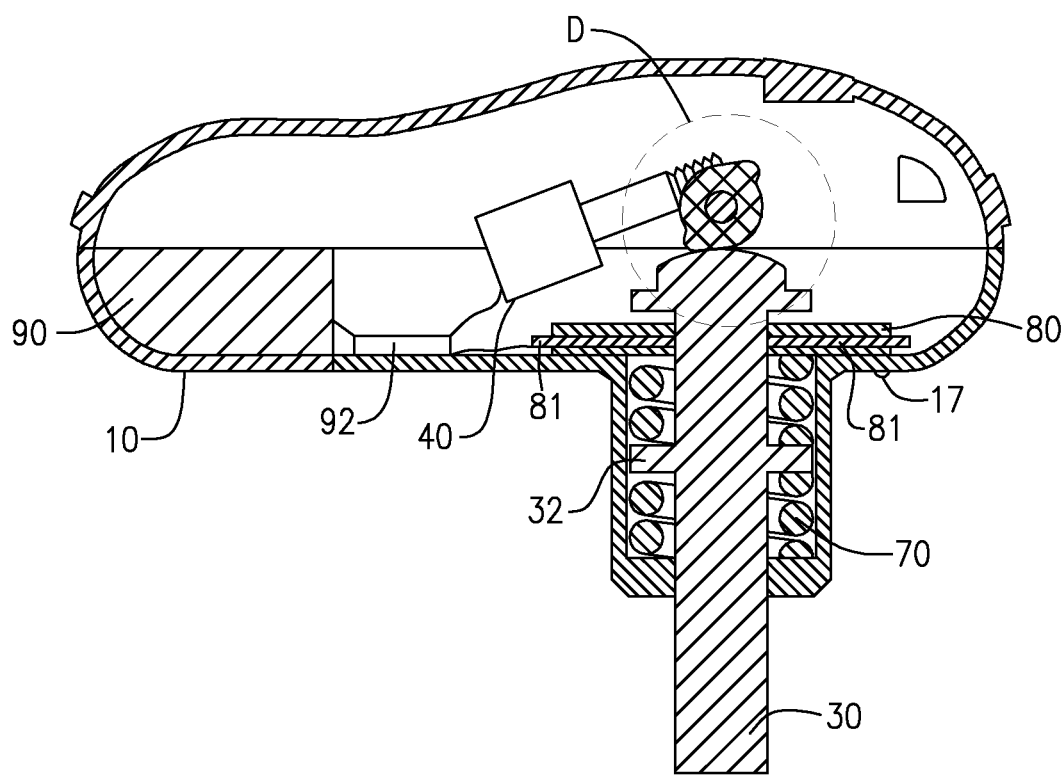
FIG. 4 is cross-sectional view of the device according to FIGS. 1 and 1A, taken along the line B-B of FIG. 3.

Now referring to FIGS. 4 and 4A, motor 40 operates in a similar fashion, employing drive shaft 42 coupled with cam shaft 50 and cam 52. With further reference to FIG. 6A, in one embodiment drive shaft 42 is operably connected to cam shaft 50 using a worm gear arrangement. Cam 52 is operable to rotate such that one of lobes 52a, 52b strikes ram surface 39 to drive ram 30 in a downward direction. Spring 70 provides a restoring force as described above. Continued rotation of the lobed cam 52 produces a cycle of applied insertion force and subsequent recovery to a baseline position. Accordingly, and in a similar manner as described for motor 46, a pulsed application of force is produced.

As shown in FIG. 3A, the impactor 2 may include one or more sensors or load cells 64 electrically coupled to the circuit board 92 and positioned to detect impact force between cam 52 and ram surface 39 and between cam 56 and ram remover flange 37. The measured data may be displayed in display 16.

Figure 5:
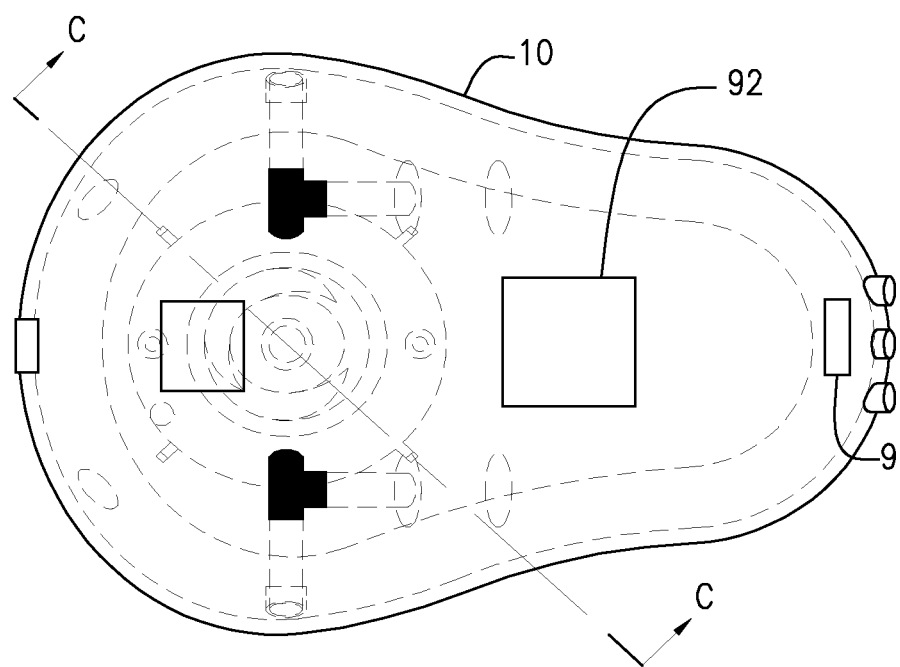
FIG. 5 is a top view of the device according to FIG. 1, with some interior components shown in phantom.
Figures 5A, 5B:
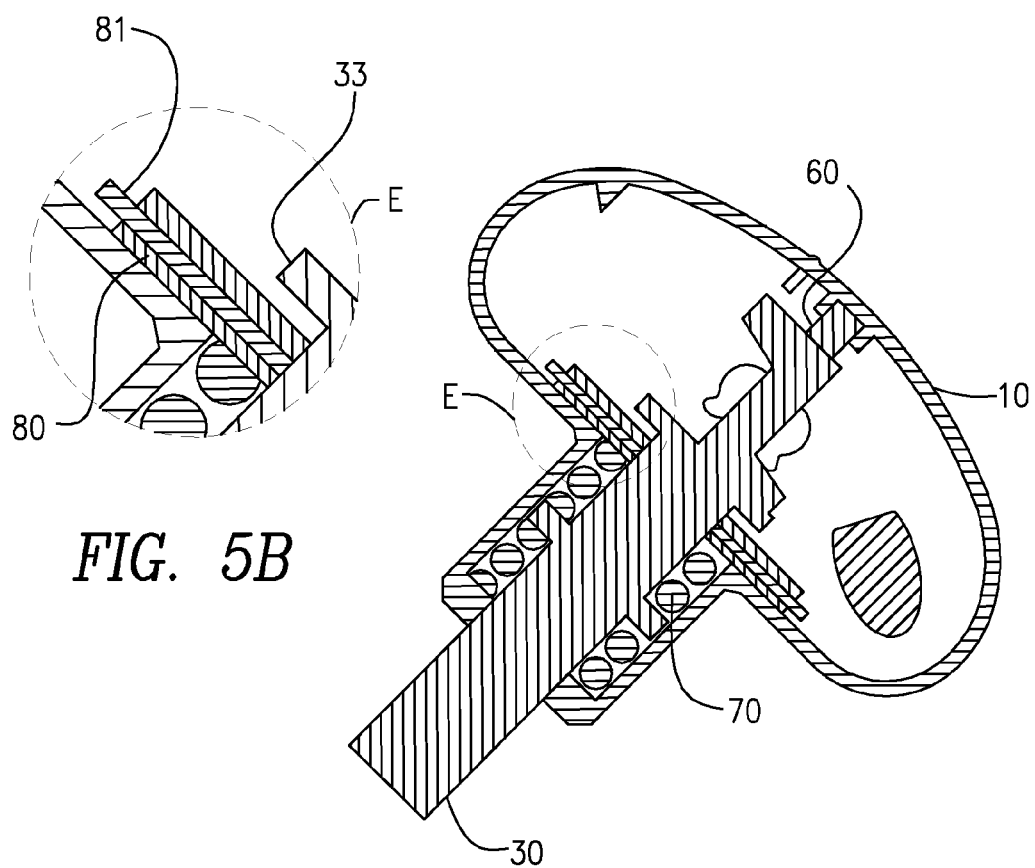
FIG. 5A is a cross-sectional view of the device according to FIG. 5, taken along the line C-C of FIG. 5.
FIG. 5B is an enlarged view of detail E of FIG. 5A according to an embodiment of the present disclosure.
Figure 6:
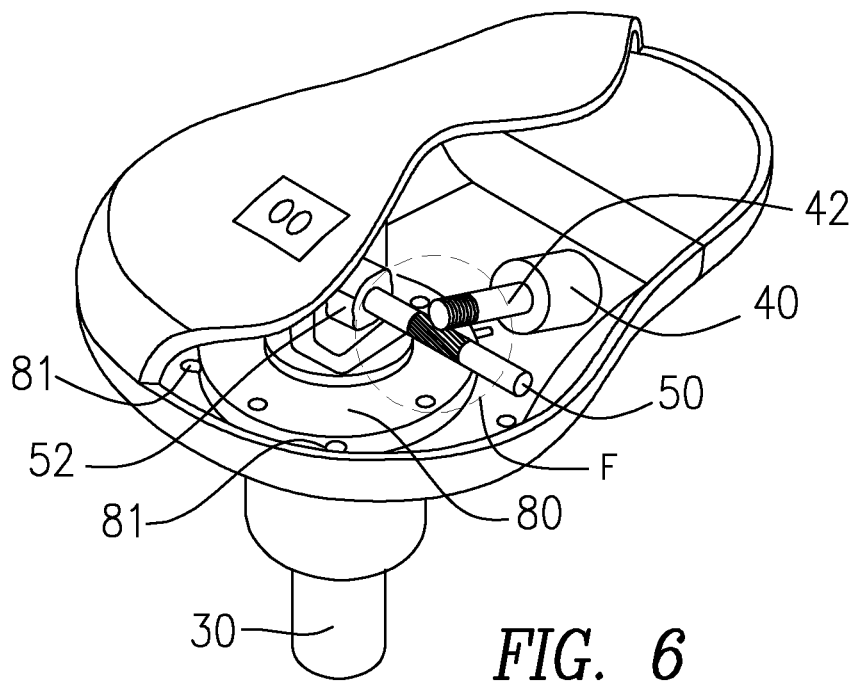
FIG. 6 is a perspective view of the device according to FIG. 1 with a portion of the top housing cut away according to an embodiment of the present disclosure.
Figure 6A:
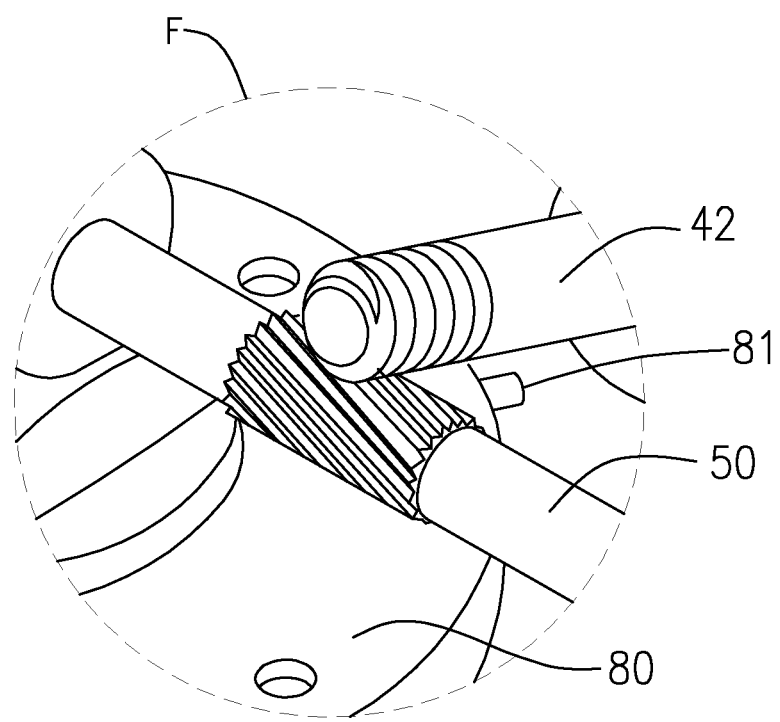
FIG. 6A is an enlarged view of detail F of FIG. 6 according to an embodiment of the present disclosure.

With further reference to FIGS. 5-6A, mounting plate 80 includes one or more strike alignment strain sensors 81 electrically coupled to circuit board 92. The strike alignment strain sensors 81 may be positioned in bores formed in the edge of the mounting plate 80, for example, bores separated by about 90 degrees along the perimeter of the mounting plate 80. The strike alignment strain sensors 81 are thus positioned to measure load applied perpendicular to the axis of the ram 30 to detect misalignment of the impactor 2. In some embodiments, depending on the programming of the circuit board 92, misalignment of the impactor 2 may produce an audible alarm, a message on the display 16, and/or cause the impactor to not operate. Suitable strain sensors include micro-gauge surface sensors available commercially from MicroStrain® of Williston, Vt.

Figure 7:
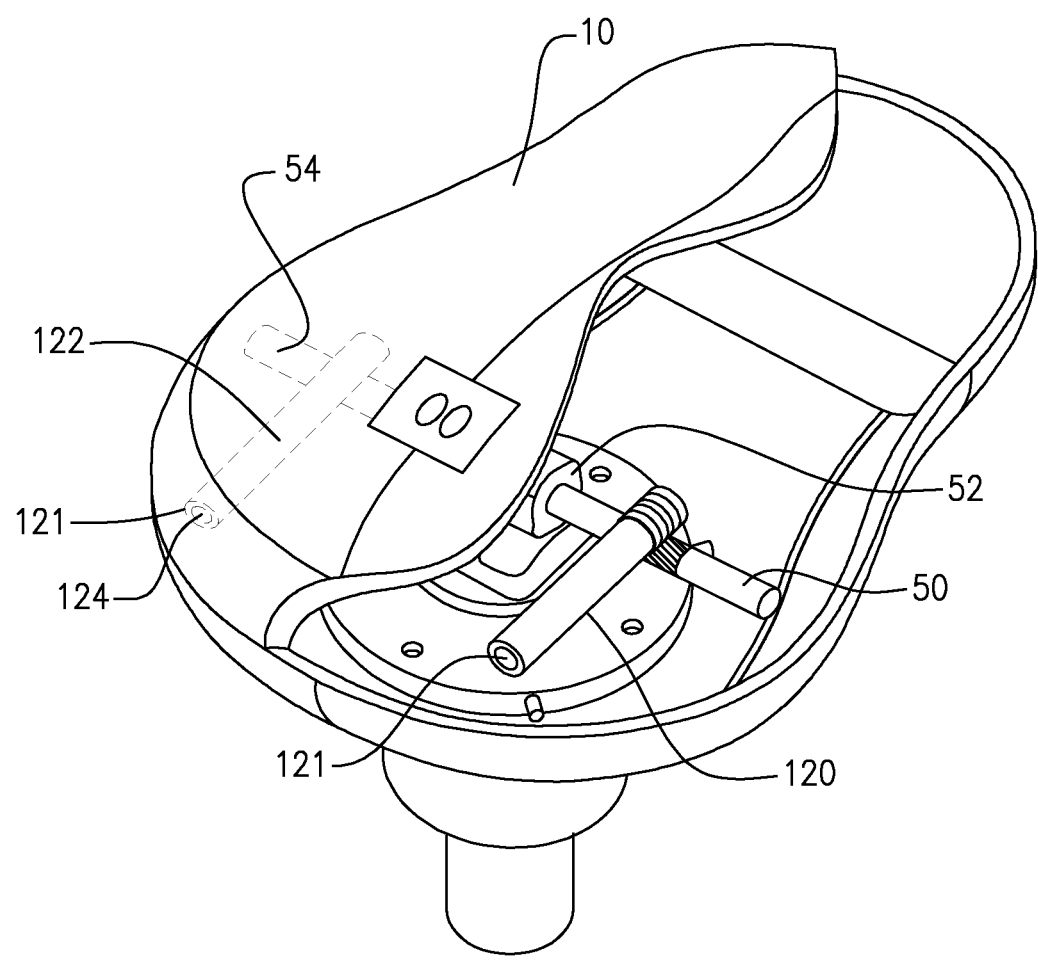
FIG. 7 is a perspective view of the device according to FIG. 1 with a portion of the top housing cut away to show a drive shaft for receiving an external drive according to an embodiment of the present disclosure.

With further reference to FIG. 7, in another embodiment the impactor 2 does not include internal motors. Rather, the impactor 2 includes drive shafts 120, 122 each axially aligned with corresponding apertures 124 formed in housing 10. The drive shafts 120, 122 each include a connector end 121 configured to connect to an external drive. Connector end 121 may be of any suitable form, including but not limited to a female element with an interior surface keyed to a corresponding male element, a bolt, quick-release coupling, etc. For example, connector end 121 may be a bore with a hexagonal cross-section for receiving a hexagonal bolt, or bit, fitted to a drive such as a powered drill. The external drive connector is connectable to one of the drive shafts 120, 122 via aperture 124, depending on the direction of operation desired.

Figure 8:
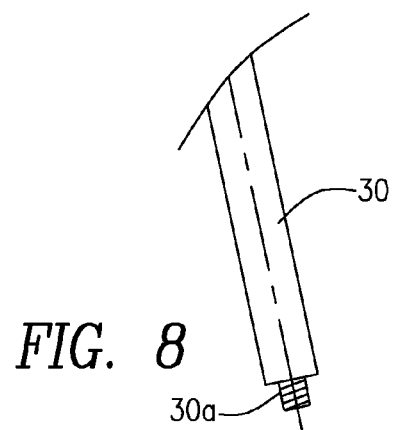
FIG. 8 is a side view of an impactor/remover ram 30 having a connector end 30a for receiving an attachment according to an embodiment of the present disclosure.
Figure 8A:
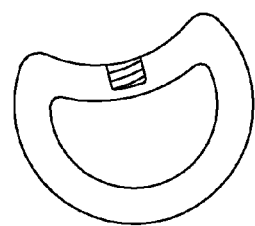
FIG. 8A is a top view of an implantable Anterior Lumbar Interbody Fusion (ALIF) device with a means to connect to an impactor/remover ram according to an embodiment of the present disclosure.
Figure 8B:
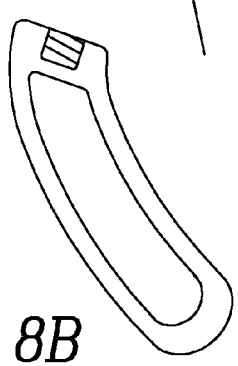
FIG. 8B is a top view of an implantable Transforaminal Lumbar Interbody Fusion (TLIF) device with a means to connect to an impactor/remover ram according to an embodiment of the present disclosure.
Figure 8C:
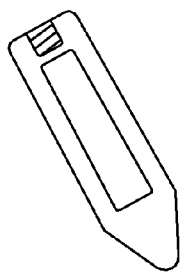
FIG. 8C is top view of an implantable Posterior Lumbar Interbody Fusion (PLIF) device with a means to connect to an impactor/remover ram according to an embodiment of the present disclosure.
Figure 9:
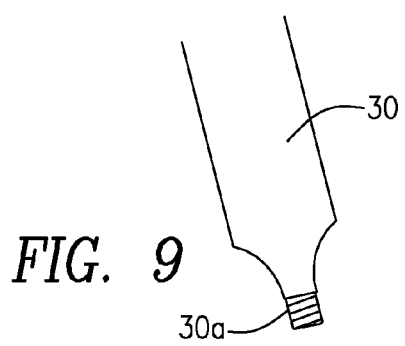
FIG. 9 is a side view of an impactor/remover ram 30 having a connector end configured to receive an attachment according to an embodiment of the present disclosure.
Figures 9A, 9B:
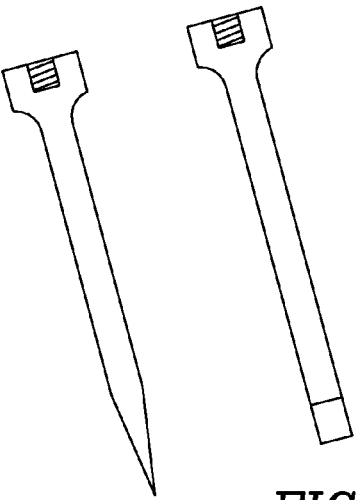
FIG. 9A is a top view of a sharp-tip distal end device with a means to connect to an impactor/remover ram according to an embodiment of the present disclosure.
FIG. 9B is a top view of a tamp distal end device with a means to connect to an impactor/remover ram according to an embodiment of the present disclosure.
Figure 9C:
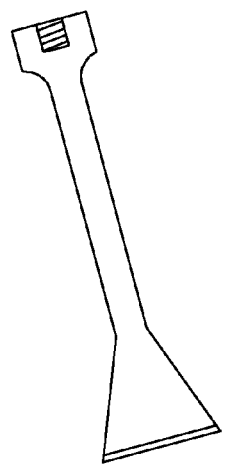
FIG. 9C is a top view of a wide chisel distal end device with a means to connect to an impactor/remover ram according to an embodiment of the present disclosure.
Figure 10:
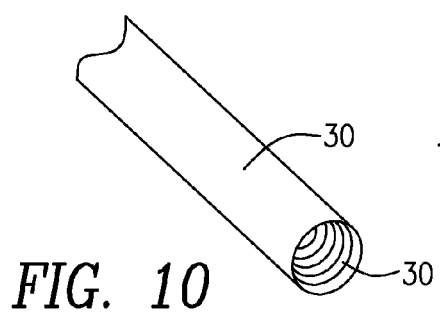
FIG. 10 is a perspective view of a threaded bore 30b for receiving an attachment according to an embodiment of the present disclosure.

With further reference to FIGS. 8-10, the ram 30 may include a connector end 30a configured to connect to a corresponding tool or implant. Connector end 30a may be of any suitable form, including but not limited to a female element an interior surface keyed to a corresponding male element, a bolt, screw, quick-release coupling, etc. Depending on the application, an attachment or implant may be connected to the ram 30, employed or inserted as needed, and disconnected from the ram 30. For example, a broaching tool may be connected to ram 30 and employed to prepare a femur for femoral stem implant in a total hip arthroplasty. The broaching tool can be removed from the impactor and replaced with a hammer attachment to assist in insertion of the femoral stem. The use of both tools is facilitated by high-frequency insertion allowing for more controlled and safer placement most likely associated with decreased injury to adjacent tissues.

In a further example, an interbody cage can be fitted to the connector end 30a and the impactor used to insert the interbody cage into in intervertebral disk space, providing for safer insertion and decreased risk of catastrophic vertebral endplate and implant failure. After proper insertion, the interbody cage is disconnected from the connector end 30a and left in place.

As will be apparent to those skilled in the art, there are many types of devices that may be attached to the ram 30. Accordingly, the foregoing examples are non-limiting.

Figure 11:
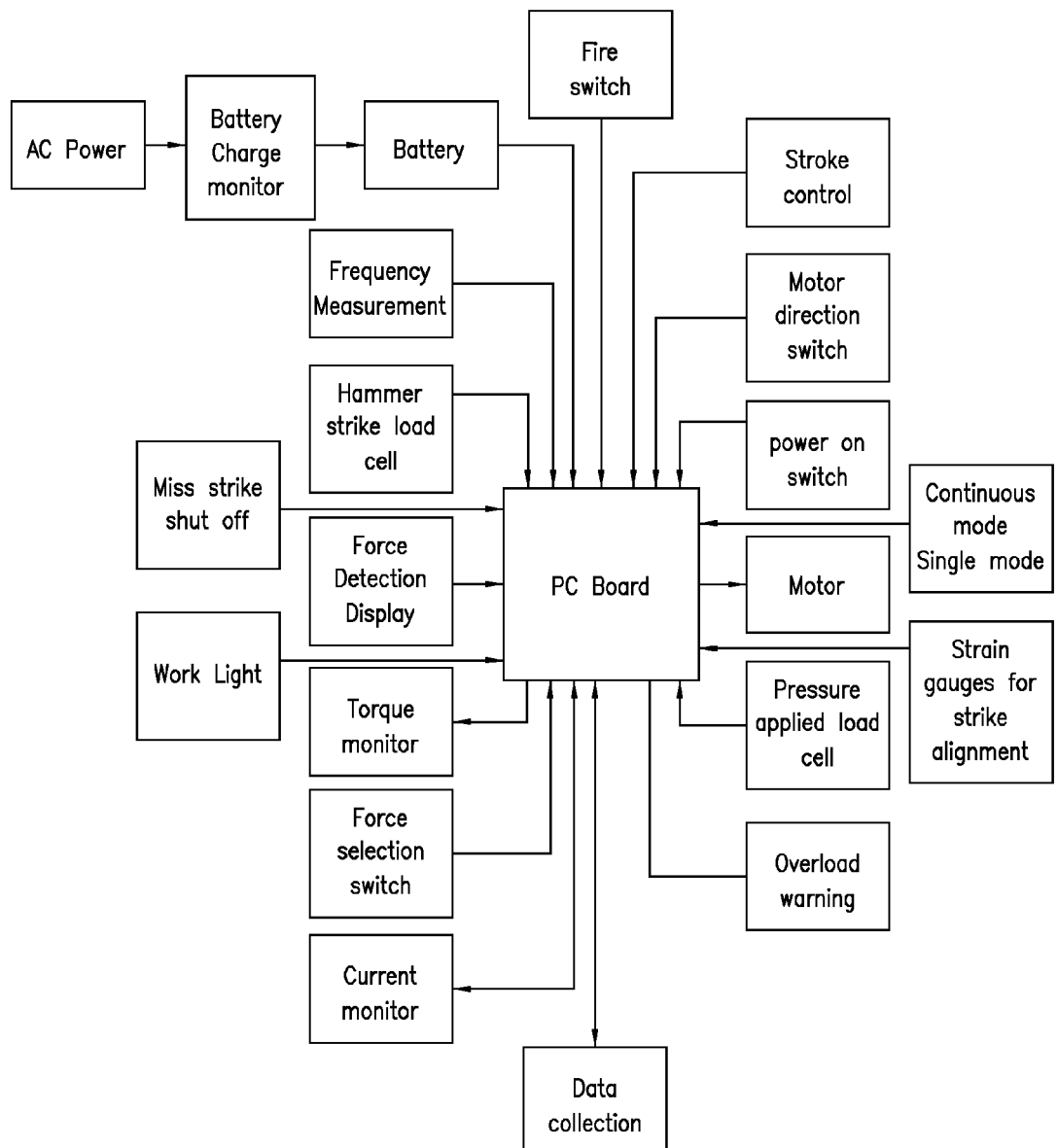
FIG. 11 is a schematic of elements coupled to a printed circuit board according to an embodiment of the present disclosure.

Now with further reference to FIG. 11, all sensors, switches and displays disclosed and discussed herein are electrically connected to the circuit board 92. Circuit board 92 is the main control hub of the device, handling commands input by virtue of the user selecting various combinations of switch positions. The circuit board 92 may include circuitry operable to measure battery charge, strike frequency, torque, current, and input from various sensors such as sensors 60 and 81 and output data for display on display 16. The circuit board 92 may include a processor and memory to capture data for output to an external computer, server or storage device. For example, the data from sensors 81 and 60, as well as from other sensors and detectors, may be saved in a memory, which may be part of a processor disposed on circuit board 92. USB port 9 (FIG. 5) may be disposed in housing 10 and operable for downloading stored data saved in a memory. The circuit board 92 may include a wireless card and communication means to transmit data wirelessly to a server or other computer. In either case, the data is saved and may be reviewed by the user, surgical team or others.

Figure 12:
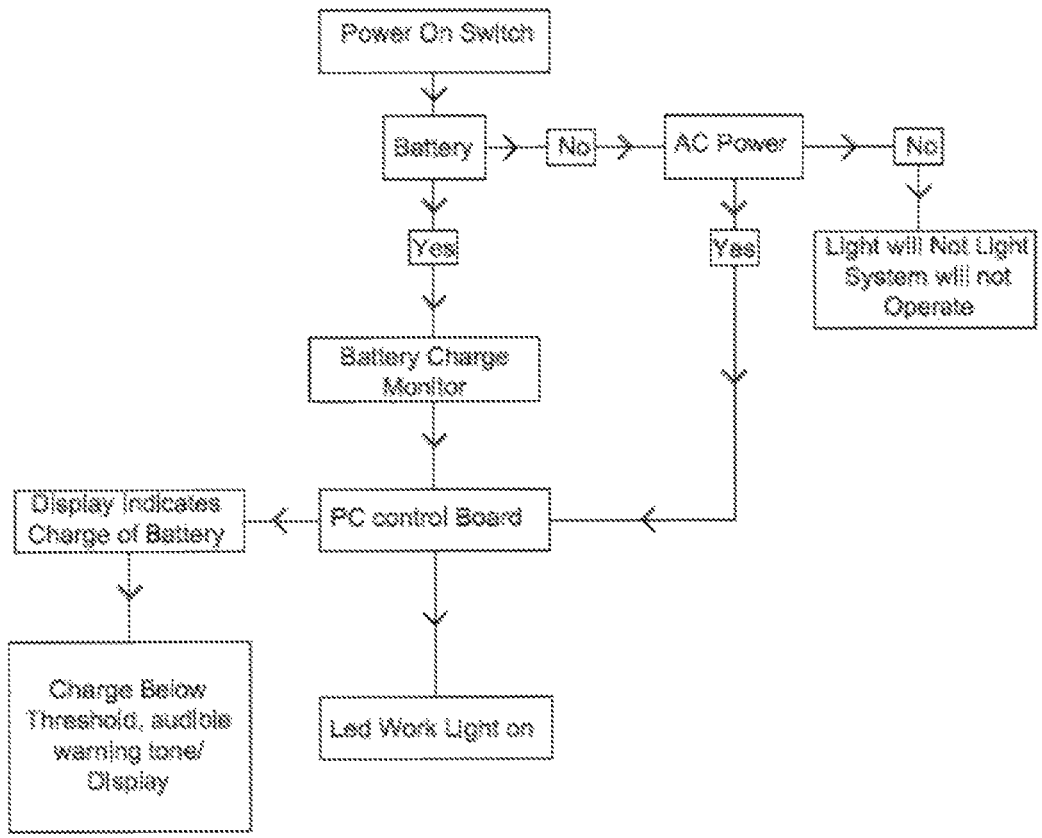
FIG. 12 is a schematic of elements controlled through a printed circuit board according to an embodiment of the present disclosure.

In one embodiment display 16 is operable to display data monitored by the printed circuit board 92 concerning the impactor 2 such as but not limited to battery life, "ready" signal that the device is ready to use, frequency, force applied, overload warning, current, strike alignment, and torque Further referring to FIG. 12, in some embodiments the power switch 19 makes power available to the impactor 2 so that it can run. However, in some embodiments, adjusting the power switch 19 to the "on" position will not cause the impactor to begin operating. In some embodiments, the impactor will only operate if the power switch is turned "on" and the fire switch 11 is activated. In some embodiments, when the power switch 19 is turned "on" the work light 17 illuminates and/or display 16 indicates the impactor is ready to use. In the event the circuit board 92 detects a low battery charge, the circuit board 92 may cause an audible warning tone to issue, and/or cause the display 16 to show a low battery message.

Figure 13:
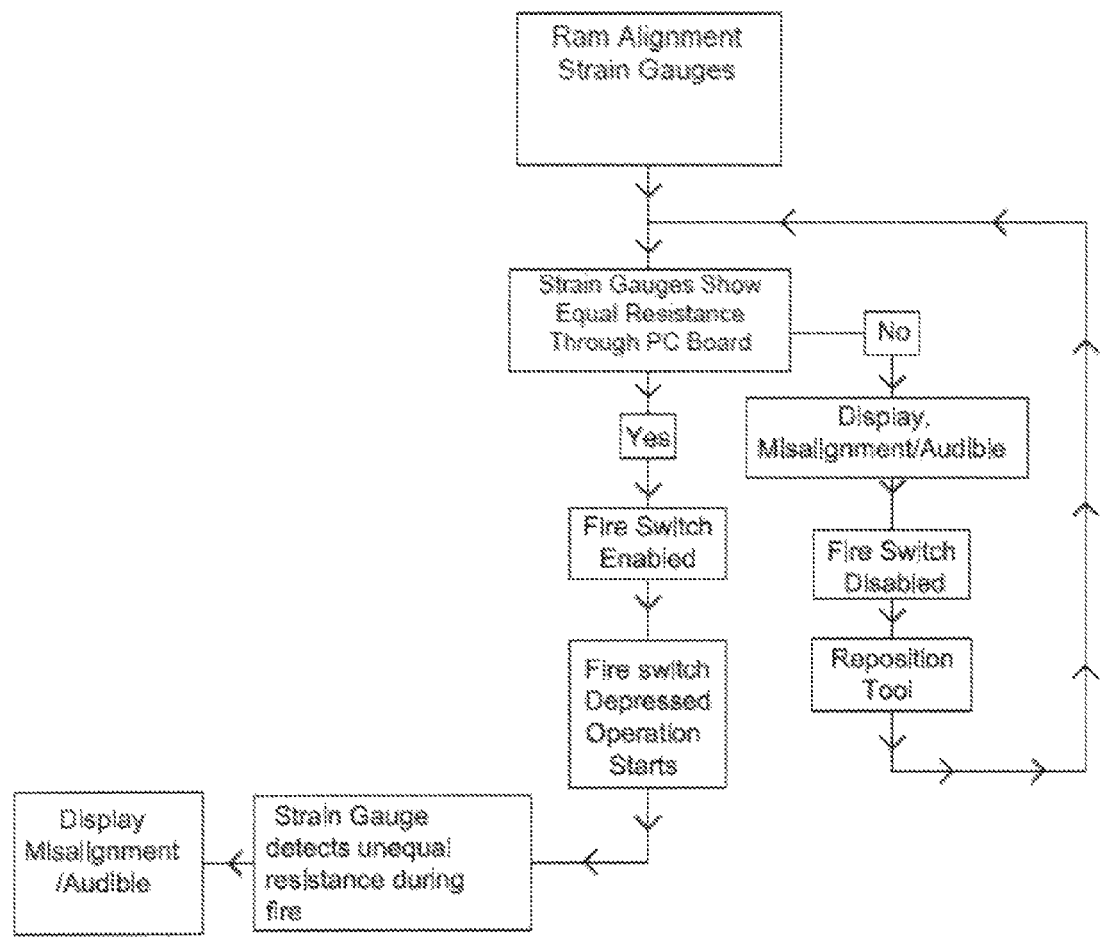
FIG. 13 is a schematic of elements controlled through a printed circuit board according to an embodiment of the present disclosure.

With reference to FIG. 13, strain alignment gauges 81 measure and report strain measurements to the circuit board 92. If the measurements from the strain gauges 81 reveal equal resistance, the fire switch 11 is enabled and actuation of the fire switch 11 will start the impactor 2. If the data from the strain alignment gauges reveal unequal force distribution, in some embodiments, depending on the programming of the circuit board 92, misalignment of the ram is deemed present and the impactor 2 may produce an audible alarm, a message on the display 16, and/or cause the impactor to not operate by disabling the fire switch 11. In one embodiment, the circuit board 92 includes programming to override the disabled fire switch by the placing the stroke direction control switch 22 in a neutral position and depressing the fire switch 11 rapidly a given number of times, such as from 3-6 consecutive times. In another embodiment the override command can be canceled by cycling the power switch 19 off then on.

Figure 14:
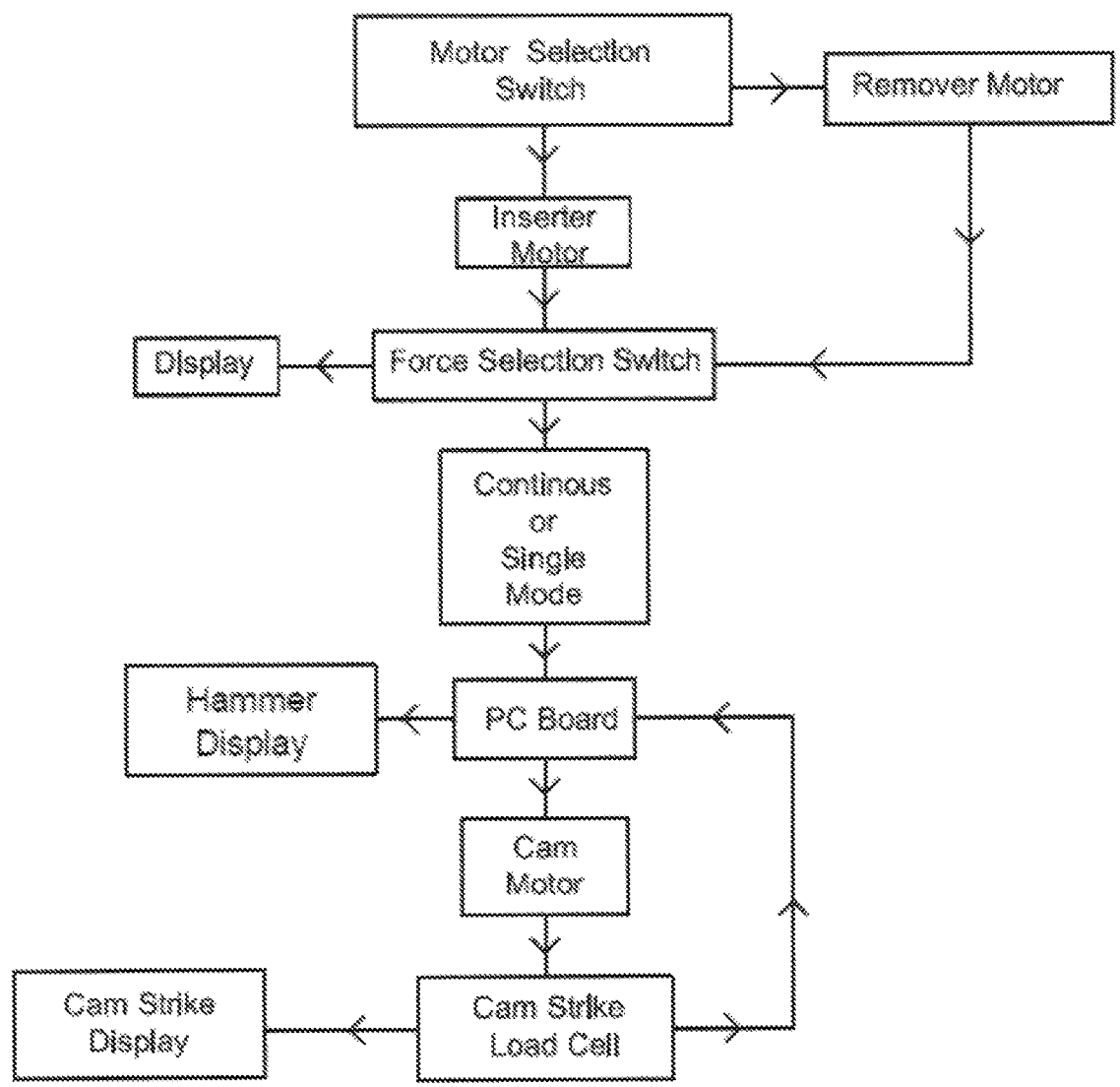
FIG. 14 is a schematic of elements controlled through a printed circuit board according to an embodiment of the present disclosure.
Figure 15:
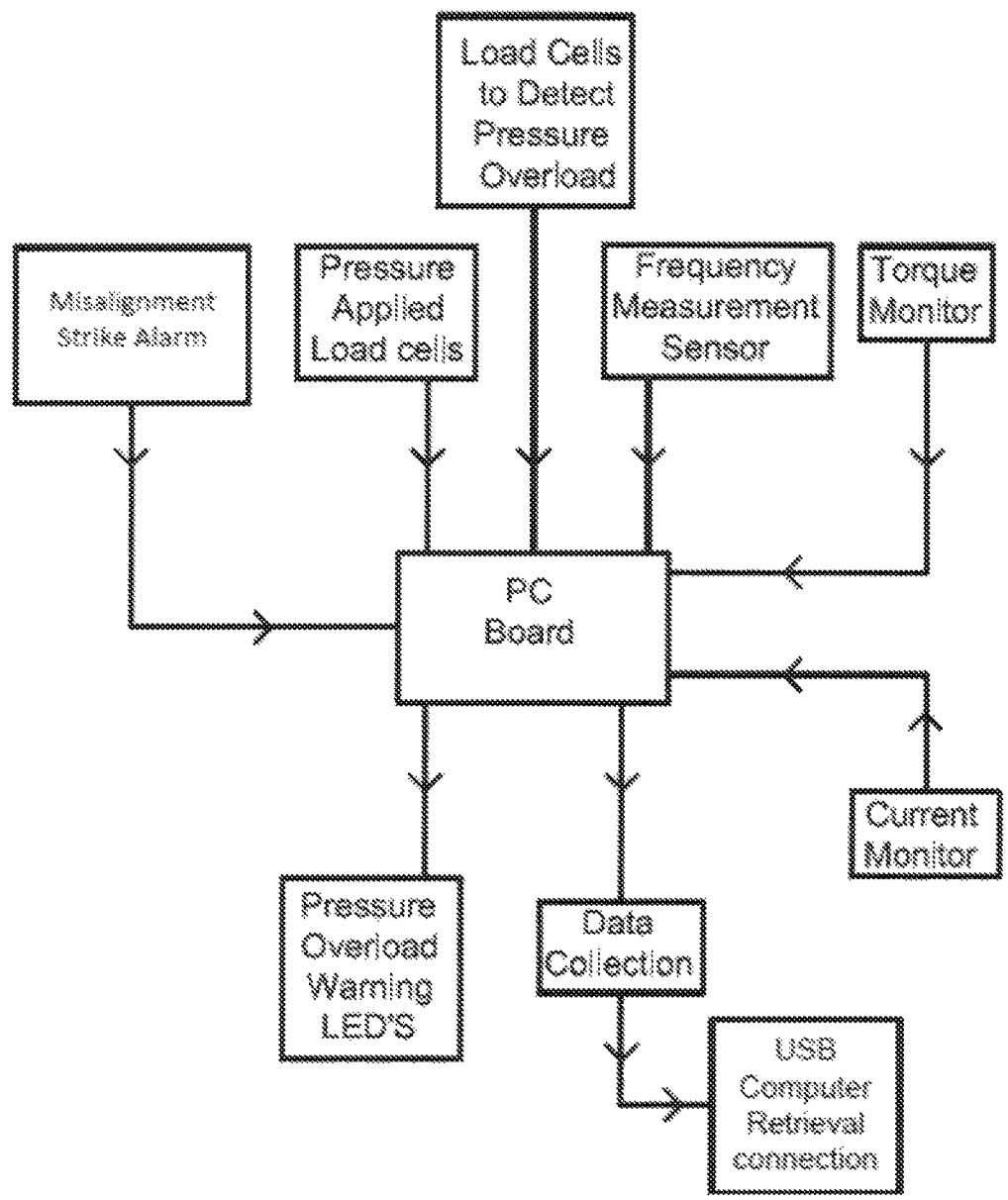
FIG. 15 is a schematic of elements controlled through a printed circuit board according to an embodiment of the present disclosure.

With reference to FIG. 14, the stroke direction control (or motor selection) switch 22 permits a user to select the stroke direction of the impactor, i.e., removal or insertion mode. Adjusting the stroke direction control switch 22 to the "remover" position causes the impactor to deploy the remover motor 46 when the power switch 19 is in the on position and the fire switch 11 is in the "on" position. Similarly, adjustment of switch 22 to the "inserter" position causes the impactor to deploy the inserter motor 40 when the power switch 19 is in the on position and the fire switch 11 is in the on position. The display 16 may display the motor that is selected. As shown in FIG. 3A, the impactor 2 may include one or more sensors or load cells 64 electrically coupled to the circuit board 92 and positioned to detect impact force between cam 52 and ram surface 39 and between cam 56 and ram remover flange 37. The measured data may be displayed in display 16.

In one embodiment, the stroke direction control switch 22 is a three-position switch. When the switch is in the center, or neutral, position the impactor 2 will not fire. This allows the user to position the impactor 2 before the work begins. When the stroke direction control switch 22 is moved to either the "insert" or "remover" position, the work zone light 17 will illuminate to add extra light to the operation being performed.

The amount of force that is delivered by the cams 52, 56 may be selected by the user by adjustment of the force selection switch 18. In one embodiment the force adjustment switch 18 is operable to move between selectable positions to vary the speed of the motor that is being employed. The force selection switch 18 may operate by limiting the current to the motors and thereby the striking force of the cams. As will be apparent to the skilled artisan, the number of selectable positions for the force adjustment switch 18 are a matter of design choice. In some embodiments, the number of settings is from 1 to 100. In other embodiments the number of settings is from 2 and 10. In still other embodiments the number of settings is from 3 to 8. In some embodiments the setting of the force selection switch 18 may be displayed in the display 16 for ease of reference for the user. The switch 18 may be a push button that permits a user to scroll the force settings, increasing or reduce the force by repeated depressions of the switch 18. In one embodiment, where the force selection switch 18 is a push button, depressing the button once causes the display 16 to display a power bar graph identified from 30 to 100%. A subsequent push of the button causes the display to show an increase by a given interval, such as but not limited to 10%. If no further actuations of the switch 18 are made within a given interval of time, for example, five seconds, the setting displayed is retained in the processor. The circuit board may be programmed to provide a default value on start-up of the impactor 2. In one embodiment the default value is 30%.

The continuous mode/single mode switch 20 is adjustable to permit a user to select the mode of operation of the impactor 2. In the single mode the impactor produces one strike per activation of the fire switch 11. In the continuous mode the selected motor will continue to operate while the fire switch 11 is depressed. The position of the continuous mode/single mode switch 20 may be displayed on display 16.

Thus, the impactor 2 may in single mode operate at a frequency decided by the user, i.e., the frequency is the desired interval between actuations of the fire switch 11. Depending on the position of the force selection switch 18, the amplitude of each single mode pulse can be low, high or somewhere intermediate. In continuous mode, the frequency and amplitude can be varied simultaneously.

With further reference to FIG. 15 and FIGS. 2, 3 and 3A, multifunction sensor 60 is positioned between the proximal end of the ram 30 and the housing 10 and electrically coupled to circuit board 92. Multifunction sensor 60 includes a plurality of load cells, including but not limited to hammer strike load cells and applied pressure load cells to detect the actual force that is distributed from the cams 52, 56 to the ram 30, and/or from the pressure exerted on the impactor 2 by the user. In some embodiments, depending on the programming of the circuit board, a detected force above and/or below a selected threshold may produce an audible alarm, a message on the display 16, and/or cause the impactor to not operate. Suitable multifunction sensors and transducers are available commercially, such as from CTS Corporation of Elkhart, Ind. or Keyence Corporation of Itasca, Ill. In some embodiments the threshold force is from 0 to 1000N.

Although the devices and systems of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. An impactor comprising: a housing comprising an upper portion and a lower portion, at least part of the lower portion extending axially from the upper portion, a ram comprising a first end positioned in the upper portion and positioned in axial alignment with the lower portion, an opposite end of the ram extending from the lower portion of the housing, at least one drive assembly comprising a first drive shaft operably coupled to a cam shaft, a cam operably coupled to the cam shaft, the drive shaft operably connectable to a motor, wherein the cam is operable to rotate and positioned to contact the proximal end of the ram upon rotation of the cam, a circuit board comprising circuitry operable to receive instructions from a plurality of switches electrically coupled to the circuit board to operate the impactor, wherein the impactor is operable to deliver low amplitude pulsed strikes to a workpiece at variable frequencies.

2. The impactor according to claim 1 comprising at least one coil spring disposed annularly within the lower portion of the housing and wherein a portion of the ram is disposed in axial alignment within the coil spring.

3. The impactor according to claim 1 comprising a battery electrically coupled to the circuit board.

4. The impactor according to claim 1 wherein the impactor is a hand-held device.

5. The impactor according to claim 1 comprising at least one motor contained within the housing and operably coupled to the drive shaft.

6. The impactor according to claim 1 comprising an inserter motor electrically coupled to the circuit board and a battery or external power source, and operably coupled to the drive shaft, wherein the ram comprises an inserter surface positioned to receive impact from the cam to drive the ram in the direction of the lower housing.

7. The impactor according to claim 1 comprising a remover motor electrically coupled to the circuit board and a battery or external power source, and operably coupled to the drive shaft, wherein the ram comprises a removal flange positioned to receive impact from the cam to drive the ram in the direction of the upper housing.

8. The impactor according to claim 1 comprising an inserter motor and a remover motor electrically coupled to the circuit board, and further comprising at least two drive assemblies, wherein each of the inserter and remover motors are operably coupled to one of each at least two drive assemblies, wherein the ram comprises an inserter surface positioned to receive impact from a first drive assembly cam to drive the ram in the direction of the lower housing, and wherein the ram comprises a removal flange positioned to receive impact from a second drive assembly cam to drive the ram in the direction of the upper housing.

9. The impactor according to claim 8 comprising a switch electrically coupled to the circuit board operable to select which motor to operate.

10. The impactor according to claim 8 comprising a battery electrically coupled to the circuit board.

11. The impactor according to claim 1 comprising a power switch electrically coupled to the circuit board.

12. The impactor according to claim 1 comprising a force selection switch electrically coupled to the circuit board.

13. The impactor according to claim 1 comprising a fire switch electrically coupled to the circuit board.

14. The impactor according to claim 1 comprising a switch electrically coupled to the circuit board operable to control the rotation of a cam between a single rotation and continuous rotation.

15. The impactor according to claim 1 comprising a mounting plate mounted to the lower housing having an opening formed therein in which the ram is disposed, the mounting plate comprising at least one sensor electrically coupled to the circuit board, the at least one sensor operable to detect misalignment of the ram.

16. The impactor according to claim 1 comprising a sensor electrically coupled to the circuit board and positioned to detect force imparted by the cam on the ram.

17. The impactor according to claim 1 comprising a sensor electrically coupled to the circuit board and positioned to detect force imparted by a user on the impactor.

18. The impactor according to claim 1 comprising a display electrically coupled to the circuit board operable to display data.

19. The impactor according to claim 1 wherein the ram comprises a connecting element positioned at a distal end operable to connect a tool or implant.

20. The impactor according to claim 1 wherein the drive assembly comprises a drive shaft having a connecting element disposed on an end opposite an end coupled to the cam shaft, the connecting element operable to connect the drive shaft to an external drive.

* * * * *